(12) United States Patent
Clarot et al.

(10) Patent No.: US 9,072,673 B2
(45) Date of Patent: *Jul. 7, 2015

(54) METHOD FOR MEASURABLY IMPROVING ORAL HEALTH

(75) Inventors: Tim Clarot, Phoenix, AZ (US); Regina Miskewitz, Phoenix, AZ (US)

(73) Assignee: ZICARE, LLC, Scottsdale, AZ (US)

( * ) Notice: Subject to any disclaimer, the term of this patent is extended or adjusted under 35 U.S.C. 154(b) by 846 days.

This patent is subject to a terminal disclaimer.

(21) Appl. No.: 12/300,995

(22) PCT Filed: May 15, 2007

(86) PCT No.: PCT/US2007/068999
§ 371 (c)(1),
(2), (4) Date: Jun. 12, 2009

(87) PCT Pub. No.: WO2007/134335
PCT Pub. Date: Nov. 22, 2007

(65) Prior Publication Data
US 2009/0257963 A1    Oct. 15, 2009

Related U.S. Application Data

(60) Provisional application No. 60/800,632, filed on May 15, 2006.

(51) Int. Cl.
| | | |
|---|---|---|
| *A61K 8/00* | (2006.01) | |
| *A61K 8/27* | (2006.01) | |
| *A61K 33/30* | (2006.01) | |
| *A61K 31/14* | (2006.01) | |
| *A61Q 11/00* | (2006.01) | |
| *A61K 8/365* | (2006.01) | |
| *A61K 8/49* | (2006.01) | |
| *A61K 8/73* | (2006.01) | |

(52) U.S. Cl.
CPC . *A61K 8/27* (2013.01); *A61K 8/365* (2013.01); *A61K 8/4926* (2013.01); *A61K 8/731* (2013.01); *A61Q 11/00* (2013.01)

(58) Field of Classification Search
USPC .................. 424/49, 401, 54, 641
See application file for complete search history.

(56) References Cited

U.S. PATENT DOCUMENTS

| | | | |
|---|---|---|---|
| 2,029,483 A | 2/1936 | Holland | |
| 3,199,510 A | 8/1965 | Sinai | |
| 4,134,511 A | 1/1979 | Deussen | |
| 4,242,323 A | 12/1980 | Vlock | |
| 4,664,906 A | 5/1987 | Sipos | |
| 4,773,548 A | 9/1988 | Deussen | |
| 4,814,163 A * | 3/1989 | Barth | 424/49 |
| 4,941,520 A | 7/1990 | Dowzall et al. | |
| 4,966,312 A | 10/1990 | Waring | |
| 5,094,845 A * | 3/1992 | Vlock | 424/52 |
| 5,246,371 A * | 9/1993 | Fischer | 433/217.1 |
| 5,578,295 A | 11/1996 | Francis et al. | |
| 5,755,572 A | 5/1998 | Bab et al. | |
| 5,948,390 A | 9/1999 | Nelson et al. | |
| 6,095,813 A | 8/2000 | Broyles | |
| 6,355,229 B1 | 3/2002 | Adamy | |
| 6,723,305 B2 * | 4/2004 | DePierro et al. | 424/54 |
| 6,861,049 B2 * | 3/2005 | Harwood | 424/49 |
| 6,932,604 B2 | 8/2005 | Han et al. | |
| 7,306,121 B2 | 12/2007 | Ophardt et al. | |
| 2001/0031170 A1 | 10/2001 | Voiers et al. | |
| 2003/0003059 A1 | 1/2003 | Dana | |
| 2004/0037789 A1 * | 2/2004 | Moneuze et al. | 424/49 |
| 2004/0131559 A1 | 7/2004 | Hauck | |
| 2005/0026107 A1 * | 2/2005 | Mongtomery | 433/89 |

FOREIGN PATENT DOCUMENTS

| | | |
|---|---|---|
| GB | 337383 A | 10/1930 |
| GB | 2210264 A | 6/1989 |
| WO | 9015592 A | 12/1990 |
| WO | WO 9015592 A1 * | 12/1990 |
| WO | 9639995 A | 12/1996 |
| WO | 03075865 | 9/2003 |
| WO | 2004071321 | 8/2004 |

OTHER PUBLICATIONS

Stookey et al., A 6 month clinical study asessing the safety and efficacy of two cetylpyridinium chloride mouthrinses, American Journal of Dentistry, 2005, 18, Special Issue, pp. 24A-28A.*
University of Iowa Health Science Relations, Saliva: It Protects Our Mouth, Jun. 2003, www.unihealthcare.com/topics/medicaldepartments/dentistry/saliva/index.html.

(Continued)

*Primary Examiner* — Lezah Roberts
(74) *Attorney, Agent, or Firm* — Snell & Wilmer L.L.P.

(57) ABSTRACT

A composition for measurably improving oral health, a system including the composition, a method of using the composition and system, and a method of forming the composition and system are disclosed. The composition is a gel that maintains contact with a portion of an oral cavity for an extended period of time to, for example, prevent or reduce plaque and calculus buildup. The system includes a composition and a container encapsulating the composition. The composition is applied by rupturing the container and applying the composition through the ruptured portion of the container. In exemplary embodiments, the methods, systems and kits disclosed herein are suitable for measurably reducing an amount of gingivitis, periodontitis, bleeding, plaque and/or tartar.

20 Claims, 6 Drawing Sheets

(56) References Cited

OTHER PUBLICATIONS

Anonymous, "The Importance of Oral Hygiene," Product Presentation for C.E.T. Rinses and Gels, http://web.archive.org/web/20050207022050/http://www.virbac.co.nz/ArticleDisplay.asp?item=68>, Feb. 7, 2005.

Anonymous, "Rinsing Product," C.E.T. Home Dental Care, http://web.archive.org/web/20060211005349/http://www.cetdental.com/rinsing_products.asp>, Feb. 11, 2006.

Schiff, Thomas, "Anticalculus effect of a cetylpyridinium chloride/zinc gluconate mucoadhesive gel: results of a randomized, double-blind, controlled clinical trial." The Journal of Clinical Dentistry, Oct. 2007.

Fortune, Bruce, The International Search Report and Written Opinion dated Nov. 7, 2007.

Simon, Frederic, The International Search Report and Written Opinion dated Nov. 23, 2007.

\* cited by examiner

METHOD FOR MEASURABLY IMPROVING ORAL HEALTH

CROSS-REFERENCE TO RELATED APPLICATIONS

This application is U.S. national phase filing under 35 U.S.C. §371 of PCT/US2007/68999 file May 15, 2007 and claims priority from U.S. Patent Applicastion Ser. No. 60/800,632 which was filed on May 15, 2006.

FIELD OF INVENTION

The present invention generally relates to methods for measurably improving oral health. More particularly, the invention relates to methods for measurably reducing an amount of gingivitis, periodontitis, bleeding, plaque, tartar and/or the like.

BACKGROUND OF THE INVENTION

Unfortunately, poor oral health affects millions of people every year. Poor oral health may result in symptoms ranging from bad breath, tooth decay, and tooth discoloration, to more serious health problems, such as gingivitis, periodontitis, and even general health problems, such as heart disease, stroke, poorly controlled diabetes and preterm labor.

The presence of dental plaque, or simply plaque, in an oral cavity can lead to such oral and general health problems. Plaque can be defined as an organized, coherent, gel-like or mucoid material that includes microorganisms in an organic matrix derived from saliva and extracellular bacterial products such as glucans, fructans, enzymes, toxins, and acids. Plaque may also contain other cells, such as desquamated epithelial cells, and inorganic components, such as calcium and phosphate. In general, dental plaque is a bacterial accumulation. Generally transparent and sticky, plaque accumulates around the teeth at the cervical margin, and then grows apically.

Once plaque forms on a surface, the plaque resists removal, and usually can be removed only by mechanical means, such as, for example, by brushing and flossing the affected areas. If not removed, however, the presence of plaque can give rise to tartar formation, gum bleeding, tooth decay, gingivitis, periodontitis, and other health problems.

Tartar is a hard, calcified plaque material that exhibits a yellowish or brownish color. Tartar forms as a result of minerals (e.g., those present in saliva and gum pockets) reacting with plaque material to form a rough calculus. Calculus generally arises from the nucleation of calcium phosphate, often in areas where the large salivary gland ducts secrete their saliva. As such, calculus can form on surfaces not covered by the oral mucosa (supragingival) or on surface located apical to the soft tissue margin of the gingiva (subgingival).

Tartar adheres to hard surfaces such as enamel, roots, and dental devices, such as orthodontia (e.g., braces), dentures, bridges, crowns, fillings, and the like, and is generally more difficult to remove than plaque. Brushing and flossing are normally not sufficient to remove tartar from a surface. If left untreated, tartar buildup can be problematic in several regards. For example, the rough, porous surface of tartar serves as a breeding ground for additional bacteria, which can calcify and form additional tartar. The bacteria growth can, in turn, lead to gum bleeding, tooth decay, gingivitis, periodontitis, and other health problems.

Gingivitis is the beginning stage of periodontitis and is often caused by the long-term effects of plaque and tartar buildup. Gingivitis is often characterized by red, swollen gums. A periodontal probe will often measure about 3 mm to about 5 mm in depth into the space between the teeth and gums at the early stages of gingivitis. At this stage, gingivitis can often be reversed with proper treatment.

Left untreated, gingivitis will likely progress to advanced periodontitis. At this stage of gum disease, plaque and tartar are typically present supragingival and subgingival and an infection has destroyed bone around a tooth. In general, at this stage, a family of chronic inflammatory infections are affecting the supporting tissues of the dentition. Teeth often become loose, and the pocket depth may range between about 5 mm and about 8 mm at this stage.

In addition to the health concerns, tartar is a cosmetic problem due to its discoloration of teeth. Namely, teeth can become yellowish or brownish color. Moreover, because the surface of tartar is rough and porous, the tartar absorbs colors from other sources (e.g., coffee, tea, tobacco, smoke, red wine and the like), and thus the presence of tartar exacerbates cosmetic tooth discoloration typically associated with such other sources.

Typical methods of preventing tartar buildup include brushing with a tartar control toothpaste. Although such toothpastes, if used regularly, may prevent buildup of additional tartar, the toothpastes are not thought to be effective at removing existing tartar from tooth enamel and dental device surfaces.

Methods of removing existing tartar typically include scaling or root planing, both of which are performed by dentists or hygienists with the aid of specialized tools. Although these techniques work well, they are relatively expensive and time consuming. Furthermore, various methods for inhibiting tartar may cause damage to tooth enamel and/or to dental devices.

Accordingly, improved methods for measurably reducing an amount of gingivitis, periodontitis, bleeding, plaque, tartar and/or the like are desired.

SUMMARY OF THE INVENTION

In accordance with various embodiments and aspects of the present invention, methods for measurably improving oral health are provided. Exemplary methods provide a relatively inexpensive and safe treatment for facilitating maintenance and improvement of oral health and/or hygiene, such as through the prevention and/or measurable reduction of an amount of gingivitis, periodontitis, bleeding, plaque, tartar and/or the like. In addition, exemplary oral health methods are relatively easy to use or perform, do not require a visit to a dentist office, and do not damage the surface of enamel or dental devices.

In accordance with various embodiments of the invention, a method of measurably improving oral health includes providing a composition and selectively applying the composition to a surface within an oral cavity.

In accordance with exemplary embodiments of the invention, a method of measurably improving oral health includes providing a system, including a composition within a container, accessing the composition, and selectively applying the composition to a surface within an oral cavity.

In accordance with further embodiments of the invention, a method of measurably improving oral health includes providing a kit, including a plurality of systems, each system including a composition within a container, accessing the composition, and selectively applying the composition to a surface within an oral cavity.

In accordance with various embodiments of the invention, the step of providing a system includes providing a viscous composition, including at least one active ingredient to promote and/or maintain oral health, and a container configured to dispense the viscous composition.

In accordance further embodiments, the viscous composition is designed to maintain the active ingredient(s) in contact with a surface for an extended period of time. Suitable active ingredients include cetylpyridinium chloride (CPC), zinc salts, other antimicrobial agents, and other ingredients to measurably improve oral health.

In accordance with yet further embodiments, the viscous composition further comprises a carrier having a thickening agent, wherein the composition is configured to maintain the active ingredient(s) in contact with a surface for an extended period of time. Exemplary thickening agents suitable for use in the viscous composition include hydroxyethylcellulose and other pharmaceutically acceptable thickeners. Exemplary compositions have a viscosity greater than about 20,000 centipoise (cp), preferably greater than about 30,000 cp, and more preferably greater than about 35,000 cp. The viscosity of the compositions may range from about 20,000 to about 250,000 cp, preferably about 25,000 to about 100,000, and more preferably about 30,000 to about 50,000 cp.

In accordance with further embodiments, the container configured to dispense the viscous composition includes an expulsion or vessel portion, configured to store and facilitate expulsion or other like transfer of the composition, and an applicator portion, configured to receive the composition and to facilitate delivery of the composition to a surface within an oral cavity. In accordance with various aspects of exemplary embodiments, the applicator portion includes an angled spout to facilitate targeted delivery of the composition—e.g., to a gum/tooth interface. In accordance with further aspects, an exemplary container is configured with an access/closure portion to maintain the composition within the container. In accordance with additional aspects of this embodiment, an exemplary container encases multiple doses of the composition. Alternatively, an exemplary container may encase a single dose. In accordance with yet further aspects, the container is configured to facilitate delivery of the composition to specific portions within an oral cavity.

BRIEF DESCRIPTION OF THE DRAWINGS

The exemplary embodiments of the present invention will be described in connection with the appended drawing figures in which like numerals denote like elements and.

Elements in the figures are illustrated for simplicity and clarity and have not necessarily been drawn to scale. The dimensions of some of the elements in the figures may be exaggerated relative to other elements to help to improve understanding of embodiments of the present invention.

DETAILED DESCRIPTION

The present invention provides methods for measurably improving oral health. More particularly, the invention provides methods of using a composition, system, and/or kit to measurably improve one or more oral health indices, such as GI, BI, PI, SI and VM-I. In general however, the methods disclosed herein are suitable for improving any oral health ailment. The methods for measurably improving oral health disclosed herein can be used to improve oral health of various animals, and are particularly well suited for humans by application to a surface of an oral cavity.

As used throughout this application, the term "surface" includes any surface on which plaque, tartar, or gum disease may form. Exemplary surfaces include teeth (both supragingival and subgingival), gums, and dental devices, such as orthodontia (e.g., braces, retainers, etc.), dentures, bridges, crowns, fillings, and the like. Further, as used herein, the term "measurably improve" means a measurable difference between an amount measured without use of the composition of the present invention and with or after use of the composition. The measurements may be compared for the same surface (e.g., before and after) or between control and test groups.

The invention is described herein in terms of various functional components, compositions and processing steps. It should be appreciated that such components, compositions and steps may be realized by any number of structural components and compositional constituents configured to perform the specified functions. For example, the methods herein may employ various compositions and containers for use with systems and kits for improving oral health indices; the specific examples as described herein are merely indicative of exemplary applications for the invention.

Figure 1:
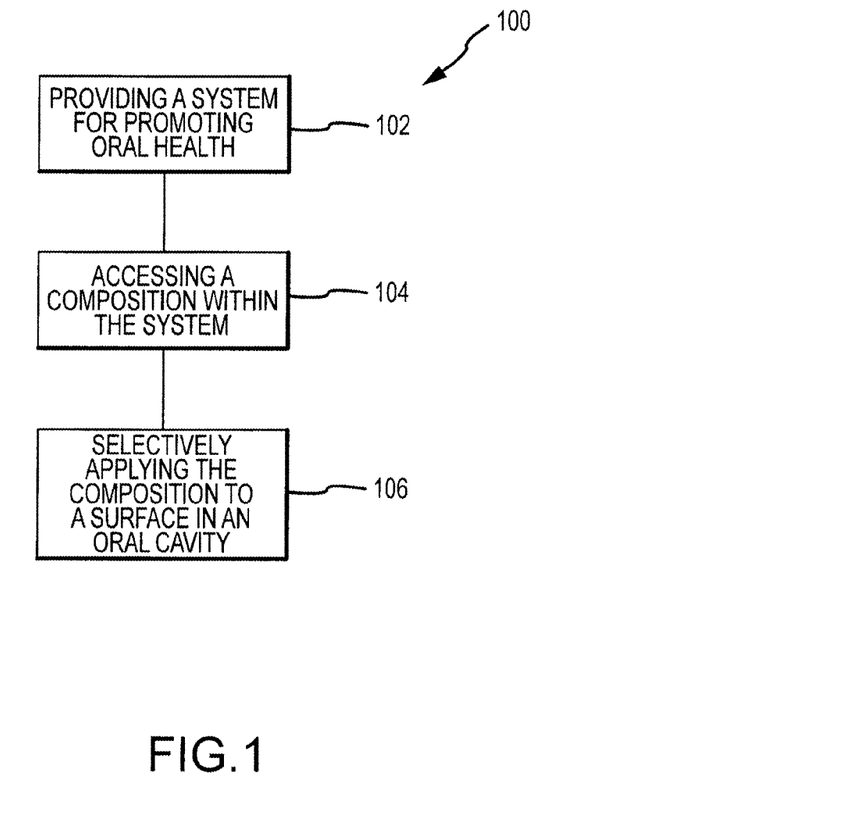
FIG. 1 illustrates a block diagram of an exemplary method for measurably improving oral health in accordance with an exemplary embodiment of the invention.

In accordance with exemplary embodiments, with reference to FIG. 1, a method 100 for measurably improving oral health includes providing a composition, system (a composition within a container), and/or kit (a plurality of systems) (step 102); accessing the composition if within a system (step 104); and selectively applying the composition to a surface within an oral cavity (step 106).

Figure 2:
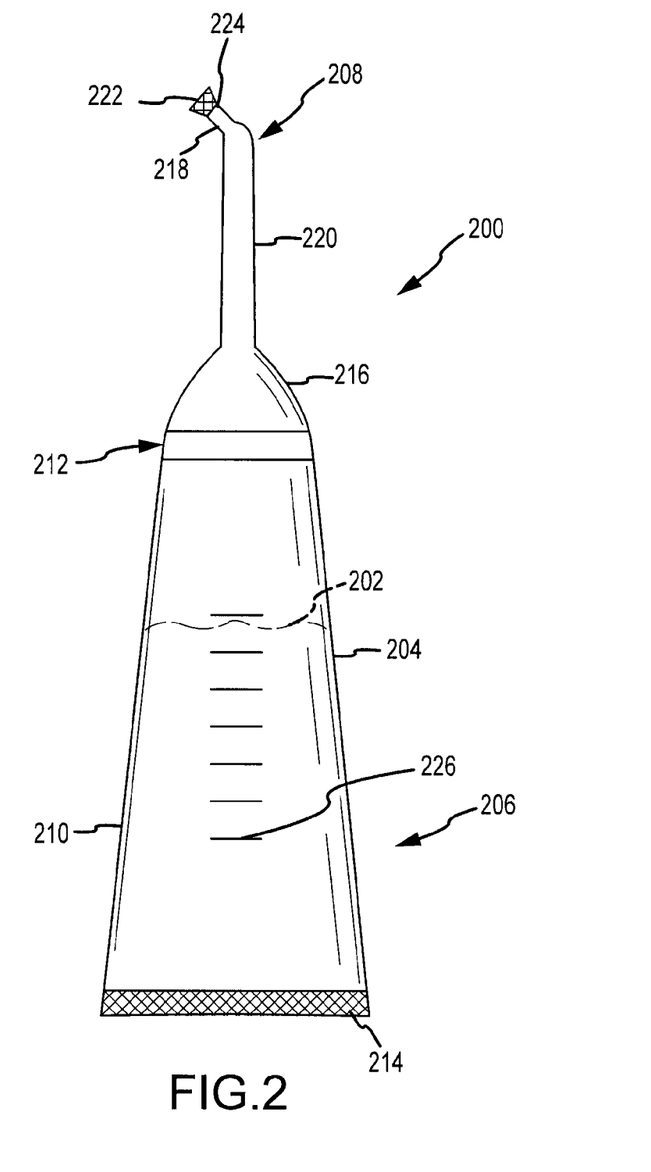
FIG. 2 illustrates an exemplary system for measurably improving oral health in accordance with an exemplary embodiment of the invention.

FIG. 2 illustrates a system 200 for use in accordance with various embodiments of the present invention. For example, system 200 can be used in connection with method 100 to facilitate prevention and/or reduction of gingivitis, periodontitis, bleeding, plaque, tartar, other general health problems and/or otherwise measurably improve oral health indices. In accordance with various exemplary aspects of the illustrated embodiment, system 200 includes a composition 202 and container 204 for selectively applying composition 202 to a surface within an oral cavity.

Figure 3:
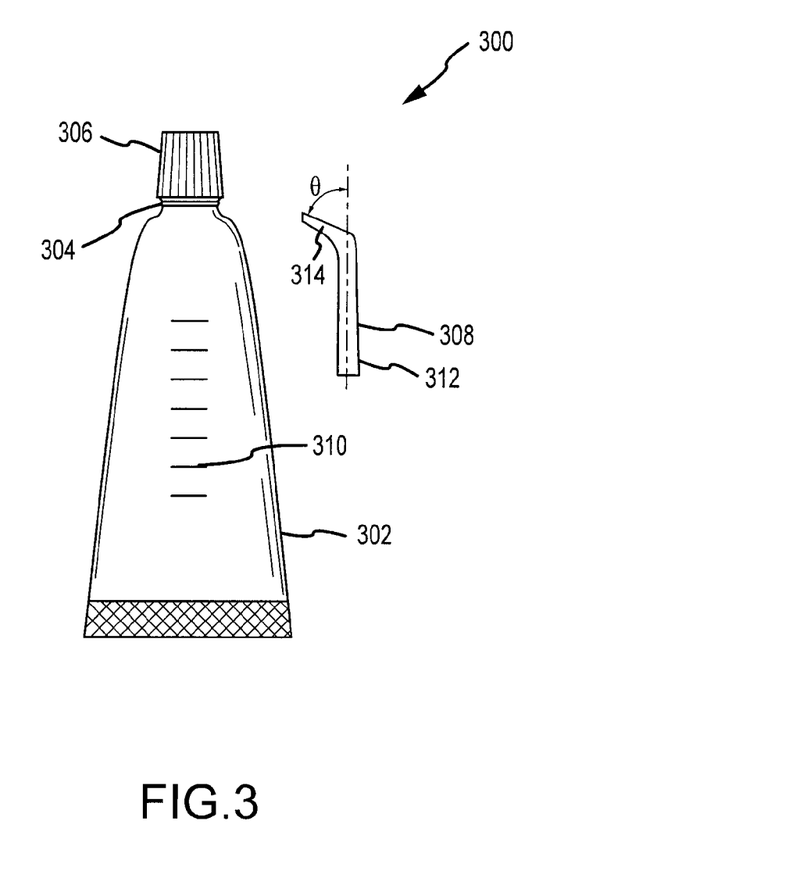
FIG. 3 illustrates another exemplary system for expulsion and application of a composition to a surface within an oral cavity in accordance with an exemplary embodiment of the invention.
Figure 4:
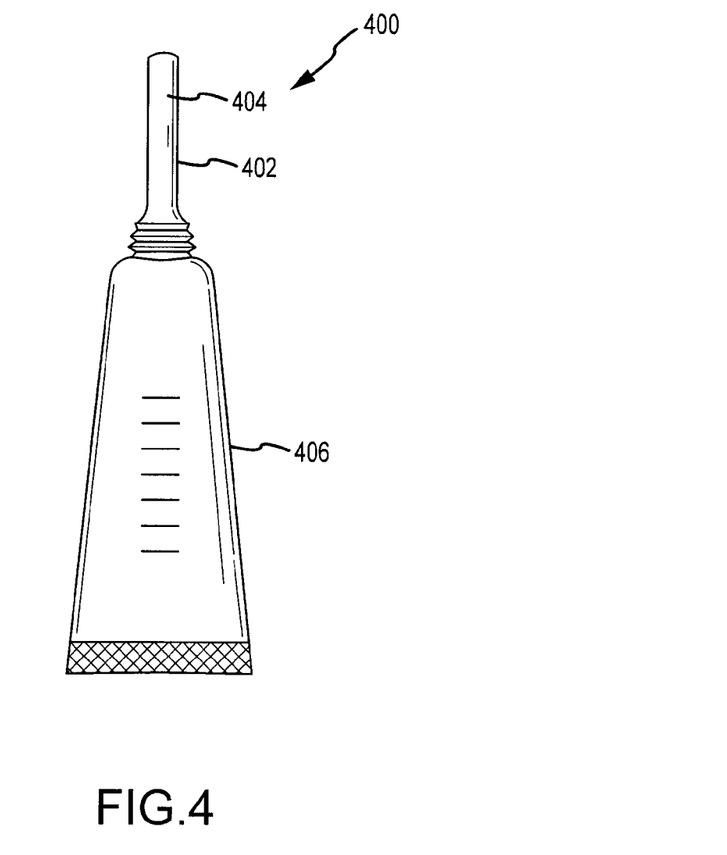
FIG. 4 illustrates yet another exemplary system for use in accordance with various embodiments of the invention.

In accordance with various exemplary embodiments, a composition (e.g., composition 202), suitable for use with systems (e.g., systems 200, 300, 400) of the present invention comprises an active ingredient and a viscous carrier. In this case, composition 202 is configured to maintain the active ingredient in contact with a surface of an oral cavity for an extended period of time to allow the active ingredient(s) to remain in contact with the surface for an extended period.

Exemplary active ingredients suitable for use with systems of the invention include one or more of the following:

cetylpyridinium chloride (CPC), dicalcium phosphate dehydrate, hydrogen peroxide, sanguinaria extract, sodium bicarbonate, sodium lauryl sulfate, sodium fluoride, stannous fluoride, sodium monofluorophosphate (MFP), zinc salts such as zinc chloride, zinc acetate, zinc citrate, zinc oxide and zinc gluconate, alkyl dimethyl amine oxide, alkyl dimethyl glycine, eucalyptol, menthol, methyl salicylate, thymol, sodium citrate, peppermint oil, sage oil, polymethylsiloxane, polxamer, and stannous pyrophosphate. Other now known or hereafter devised actives may also be used. For example, any agent, which alone or in combination is able to prevent or alleviate the severity of problems associated with dentition may be utilized. Such may include anti-caries agents and the like; agents useful in reducing tooth hypersensitivity, such as potassium nitrate, strontium chloride and/or the like; and/or plaque and calculus reducing agents, such as, for example, chlorhexidine, quaternary ammonium compounds (e.g. benzethonium chloride, domphen bromide, etc.), triclosan, herbal compounds (e.g. sanguinarine), stannous salts, complex phosphates (e.g., pyrophosphates), SLS (e.g. sodium lauryl sulfate), hydrogen peroxide, and/or the like.

An amount of the active ingredient for use within compositions suitable for uses with the invention varies in accordance with the dosage size and particular ingredient(s). In general, each active or actives selected will be used in a suitably effective amount, generally on the order of less than about 10 wt %, and more preferably 5 wt % or less. An amount of active may also be desirably selected to be within government guidelines, such as guidelines by the Food and Drug Administration in the USA. In particularly preferred compositions, the active ingredient is present in an amount of about 0.001 wt % to about 1.5 wt %, within an amount of about 0.025 wt % to about 1.0 wt %, or even within an amount about 0.05 wt % to about 0.7 wt %. All percentages set forth herein are in weight percent of the total composition, unless otherwise indicated.

In accordance with one preferred exemplary embodiment, the active ingredient(s) include CPC. In one case, CPC is present in an amount of about 0.001% to about 1%, in an amount of about 0.01% to about 0.5%, or even in an amount of about 0.05% to about 0.25% or about 0.045% to about 0.1%. In accordance with another exemplary embodiment, the active ingredient(s) also include zinc gluconate. In one case, zinc gluconate is present in an amount of about 0.001% to about 2%, in an amount of about 0.001% to about 1.5%, in an amount of about 0.01% to about 1.0%, or even in an amount of about 0.05% to about 0.75%.

In accordance with an exemplary embodiment, composition 202 also includes a thickener to obtain the desired viscosity. Suitable thickening agents include substances which increase the viscosity of composition 202, cause composition 202 to gel or coagulate, or the like, such as food-grade or pharmaceutical-grade thickeners, including, for example, hydroxyethylcellulose, hydroxypropyl methylcellulose, carrageenan, guar gum, methylcellulose, methyethylecellulose, acceptable non-ionic thickeners, and the like. The thickener may be present in an amount of about 0.01% to about 10%, in an amount of about 0.1% to about 7%, or even in an amount of about 1% to about 5% or about 0.5% to about 3%.

Composition 202 may also include a humectant such a glycerin, which may be present in an amount of about 0.01% to about 15%, preferably about 0.1% to about 10%, and more preferably about 1% to about 7%. When used, the humectant may facilitate maintaining composition 202 in a liquid form and may help maintain a desired viscosity. In accordance with specific aspects, glycerin facilitates maintaining one or more of the active ingredients in an ionic form and/or facilitates the transport of the active ingredients through composition 202.

The composition may also include a diluent. Exemplary diluents suitable for use with the present composition include sorbitol, xylitol, mannitol, water, alcohols, and oils. In accordance with particular examples of the invention, the composition includes purified water in an amount of about 80% to about 99%, preferably about 85% to about 95%, and more preferably about 88% to about 92%.

Composition 202 may also include sugar alcohols such as sorbitol and xylitol, monnital, lactitol, and the like that act as a sweetener and also as a humectant and/or emulsifier and/or diluent. When used, sorbitol or other sugar alcohol can be present in an amount of about 0.001% to about 0.5%, in an amount of about 0.01% to about 0.1%, or even in an amount of about 0.025% to about 0.075%.

Composition 202 may also include a natural or artificial sweetener such as cyclamates, sucralose, saccharin (e.g., sodium or calcium), ace-k, or aspartame which, when included in composition 202, can be present in an amount of about 0.001% to about 1.5%, in an amount of about 0.01% to about 1%, or even in an amount of about 0.25% to about 0.75%.

Colorants may also be added to composition 202. For example, composition 202 can include colorants, such that when composition 202 is applied to or proximate the gingiva, composition 202 has a color indicative of healthy gingiva— e.g., composition 202 can be pink in color. Such a composition having a color indicative of healthy gingiva can provide added incentive to users to continue using composition 202, which in turn promotes improved health care and hygiene. Colorants may be present in any desired amount. For example, the colorants may include Red #33 and/or Red #40, available from Pylam in an amount of about 0.000005% to about 1%, preferably about 0.00050% to about 0.5%, and more preferably about 0.001% to about 0.1%. Additionally or alternatively, colorants, which are indicative of flavor may be added to the composition. Examples include FD&C Blue #1, D&C Green #5, FD&C Yellow #5, and FD&C Yellow #6.

Composition 202 may also include flavorants such as cinnamon oil, clove oil, mints, anise, citrus, fruits, and the like, which, when included in the formula are present in an amount of about 0.01% to about 2%, in an amount of about 0.01% to about 1%, or even in an amount about of about 0.1% to about 0.5%.

Essential oils such as cinnamon bark oil and clove bud oil may be particularly advantageous because they exhibit additional desirable qualities. For example, cinnamon bark oil exhibits antibacterial, antiseptic, antiviral, antispasmodic, antifungal, sedative and analgesic properties and clove bud oil has local anesthetic, antiseptic, antibacterial, and stimulating properties.

Composition 202 is configured to maintain contact with a surface for an extended period of time, which has several advantages over traditional compositions. Composition 202 preferably exhibits good microadhesion, and moreover, composition 202 preferably is quite viscous. As such, in general, relatively small amounts of composition 202 and consequently the active agent(s) can be used to effectively provide oral health care or treatment. Additionally, the relatively high viscosity allows for relatively select placement of the composition on a surface.

Exemplary compositions have a viscosity greater than about 20,000 cp, preferably greater than 30,000 cp, and more preferably greater than about 35,000 cp. By way of more particular examples, the viscosity of compositions range from about 20,000 cp to about 250,000 cp, preferably about 25,000 cp to about 100,000 cp, and more preferably about 30,000 cp to about 50,000 cp, and yet more preferably about 35,000 cp to about 45,000 cp. The viscosity values as set forth herein are measured using a Brookfield, Model DV-II+ Pro viscometer, spindle #6, 10 RPM for 90 seconds at 25 C.

In accordance with other exemplary embodiments, composition 202 includes multiple active ingredients in a carrier. For example, composition 202 can include a plurality of any active ingredients and a carrier in the weight percents disclosed herein. Composition 202 may also include any of the optional ingredients, such as thickeners, sweeteners, flavorants, and colorants as set forth herein. For example, in accordance with an exemplary embodiment, composition 202 includes CPC and zinc gluconate as the active ingredients, wherein the CPC is present in an amount of about 0.001% to about 1%, in an amount of about 0.01% to about 0.5%, or even in an amount of about 0.05% to about 0.25% or about 0.045% to about 0.1%; and wherein the zinc gluconate is present in an amount of about 0.001% to about 1.5%, in an amount of about 0.001% to about 2%, in an amount of about 0.01% to about 1.0%, or even in an amount of about 0.05% to about 0.75%.

In accordance with other exemplary embodiments, composition 202 includes one or more active ingredients and a colorant indicative of healthy gingival, wherein the color of composition 202 is more than merely decorative; it also serves the function of encouraging those that use the product to continue to use the product because there is an immediate appearance, upon application of composition 202, that healthy gingival is achieved.

A pH of a composition in accordance with various embodiments of the invention is preferably between about 4-10, preferably about 4-7, and more preferably about 5-5.4.

Composition 202 may be formed by adding a humectant (e.g., glycerin) to a first mixing vessel and the adding a thickener (e.g., hydroxyethylcellulose) to the humectant and mixing until a uniform, lump-free slurry forms. The slurry should not sit for too long at this stage, or it may become cement-like in texture and viscosity. In a second mixing vessel, add a diluent (e.g., water) and add the humectant/thickener slurry slowly (over a period of a few hours) to the diluent and mix until a smooth mixture is obtained. Once the gum is hydrated, add any sugar alcohol, sweetener, and colorant to the mixture and mix until each is dissolved. Then, add a preservative and mix until dissolved and uniform. Finally, add any oils and mix until the oils are dispersed in the solution and add the actives and mix until dispersed.

Referring again to FIG. 2, container 204, for use with various embodiments of the invention, is configured for containment and temporary storage of composition 202, i.e., storage until initiation of the treatment process, and for expulsing, transferring or otherwise forcing composition 202 to a surface to achieve measurably improved oral health. Container 204 can be configured in various manners for application of composition 202 to a surface. For example, container 204 can comprise various sizes, volumes, shapes and configurations for facilitating transfer of composition 202 to a surface, depending upon, for example, the purpose for which composition 202 is being applied.

In the case of prophylaxis or reduction in gingivitis, periodontitis, bleeding, plaque, tartar, and the like, it may be desirable to have a multi-dose applicator for repeated (e.g., daily) application of composition 202. Alternatively, a single-dose applicator may be desirable for limited application (e.g., travel), or for application of composition 202 to specific problem areas, such as targeted application to diseased or infected areas or dental devices within an oral cavity.

In accordance with specific examples of various embodiments, container 204 is configured to store about seven doses, about four doses, about two doses, or about one dose. However, the invention is not necessarily limited to these container sizes.

A dose size may vary in accordance with several factors, such as the particular ingredients, the dilution of the composition, and the like. Exemplary dose sizes for purpose of illustration range from about 1 mg to about 6 mg, preferably about 2 mg to about 5 mg, and more preferably about 3 mg to about 4 mg.

With continued reference to FIG. 2, container 204 includes expulsion or vessel portion 206, configured to contain or store composition 202 and to facilitate expulsion of composition 202, and applicator portion 208, configured to receive composition 202 from expulsion portion 206 and to facilitate application or delivery of composition 202 to a selected oral cavity surface.

In accordance with particular aspects of this embodiment, portion 206 is formed of a resiliently deformable material that is capable of retaining and returning to its original shape when not under pressure. In accordance with other aspects, portion 206 is formed of material that does not return to its original shape. Exemplary resilient materials suitable for portion 206 include low density polyethylene material, high density polyethylene, medium density polyethylene, linear low density polyethylene, polyvinyl chloride, K resin, polyethylene terephthalate and copolyesters, polypropylene, surlyn, silicones and other thermostatics, metal or alloy, and the like. Portion 206 may be opaque, transparent, or semitransparent. An advantage of forming vessel portion 206 of transparent or semitransparent material is that an amount of composition 202 within vessel portion 206 can be ascertained when the portion is formed of such material. Material used to form vessel portion 206 may also include UV protection additives, colorants, or the like, and is preferably FDA-approved material.

In accordance with various embodiments of the invention, expulsion or vessel portion 206 includes resilient vial 210 and a neck 212. Resilient vial 210 acts as a reservoir for composition 202 and also facilitates expulsion of composition 202 from system 200 when pressure is applied to an external surface of vial 210. As illustrated, vial 210 may also include graduations 226 to, for example, illustrate a number of doses used and/or a number of doses remaining. Neck 212 is configured to couple applicator or spout portion 208.

Although illustrated as substantially tubular, with a sealed end 214, resilient vial 210 may be of any suitable shape or configuration. For example, vial 210 may be pyramidal, cone shaped, fluted, or have a rectangular cross section. Similarly, end portion 214 may be of any suitable shape or configuration, such as linear (e.g., a crimped or heat-sealed end) or the like. In general, preferred shapes of vial 210 conserve material used to form the vial, allow for easy dispensing of composition 202, are easy to produce, and produce relatively little scrap material during production.

Container 204 can also be configured to allow a user to suitably control the rate of expulsion into applicator portion 208. For example, in accordance with an exemplary embodiment, container 204 includes a transition region 216 to facilitate flow between vial 210 and applicator portion 208. Transition region 216 may be of any suitable shape, such as frustro-conical, fluted, semi-spherical, and the like.

Applicator portion 208 may be formed of any of the material described above in connection with portion 206. Portion 208 is suitably configured for selective and/or controlled delivery of composition 202 to a target area within an oral cavity interface 206. In accordance with various embodiments of the invention, applicator portion 208 is configured to couple (e.g., detachably or otherwise) to expulsion portion 206. Alternatively, portion 208 is configured as a molded or otherwise unitary structure with expulsion portion 206, as described in more detail below. When separately formed, portions 206 and 208 may be coupled using screwed, press-fit, clamped or other techniques to permanently, semi-permanently or removably attached portions 206 and 208.

In accordance with an exemplary embodiment, applicator portion 208 comprises a structure 220 to allow composition 202 to be forced through an applicator tip 218 and onto a surface within an oral cavity. Structure 220 may be passive and substantially rigid to allow composition to flow from portion 206 to tip 218. Alternatively, structure 220 and/or applicator portion 208 may be configured as less-rigid to allow for expulsion of any remaining composition within applicator portion 208 to be squeezed or otherwise delivered or applied by applicator tip 218 onto a surface.

As illustrated structure 220 may form an angle of about zero degrees with respect to a centerline through expulsion portion 206. Alternatively, structure 220 may form other angles, ranging from about zero degrees to about 90 degrees. In further accordance with the illustrated embodiment, tip 218 forms an angle of about 45 degrees relative to the centerline of component 220; however, tip 218 may suitably form other angles relative to component 220.

Tip 218 is generally configured to facilitate placement and controlled flow of material dispensed from system 200. Tip 218 may be substantially cylindrical. Alternatively, tip 218 may have a square, rectangular, ellipse, or other cross-sectional configuration. Tip 218 may also include a weakened section 224, which may be formed, for example, by scarring a portion of tip 218. Weakened section 224 may facilitate rupturing tip 218 at weakened section 224, which in turn allows for a predicable cross section of tip 218 and thus a relatively predictable flow of material dispensed from system 200. In accordance with one particular example, tip 218 includes a substantially constant cross-section, which makes the flow more predictable, even if tip 218 is ruptured away from weakened area 224.

End portion 222 forms a sealed end at one end of tip 218. In accordance with various embodiments of the invention, end portion 222 is flat and wider at an exterior portion than an interior portion, such that end portion 222 is wider in at least one direction than tip 218. Having end portion 222 wider than tip 218 allows a user to grip end 222 to, for example, tear or sever tip 218 at weakened section 224. However, end 222 may be alternatively configured as, for example, a semisphere or other suitable shape. Alternatively, tip 218 and end portion 222 may be configured, such that end 222 can reattach to tip 218.

Spout portion 208 may be formed using a variety of materials, such as any of the materials described above in connection with vessel portion 206. However, because spout portion 208 may be formed separately from vessel portion 206, it need not be formed of the same material.

In accordance with one embodiment of the invention, vessel portion 206 and spout portion 208 are configured to sealably (and optionally rotatably) couple to each other. In the illustrated embodiment, portion 206 and 208 are threadedly coupled to each other. In accordance with other embodiments, one of portions 206 and 208 includes a protrusion and the other of portion 206, 208 includes a recess to receive the protrusion, such that the protrusion and recess hold vessel portion 206 and spout portion 208 together, while optionally allowing the two portions to rotate about an axis, with respect to each other. In accordance with another embodiment of the invention, portions 206, 208 are configured to allow vessel portion 206 and spout portion 208 to be detachably coupled to each other. In this case, neck 212 and spout 208 may be snap-fit together as described above, or portions 206 and cap 208 may engage using lug or interference-fit technology to sealably attach to each other.

FIG. 3 illustrates another system 300 for use in accordance with additional embodiments of the invention. As illustrated, system 300 includes a vessel portion 302, including a neck 304, a cap 306, and a detachable applicator 308. System 300 is similar to system 200, except system 300 includes resealable cap 306 and detachable applicator 308, rather than applicator portion 208. System 300 may be formed of any of the materials noted above in connection with system 200, and may include graduations 310 to indicated a number of doses used and/or a number of remaining doses, as described above.

Cap 306 can be removably attached to vessel portion 302 using a variety of techniques. For example, cap 306 may be threadedly attached to portion 302. Alternatively, cap 306 and portion 302 may be coupled using snap-fit, lug, interference-fit technology, or similar technologies. In accordance with one specific example of this embodiment, neck 304 includes exterior threads and cap 306 includes interior threads to threadedly engage with neck 304.

Similarly, applicator portion 308 may couple to vessel 302 in a variety of ways, such as threaded, snap-fit, lug, or similar type connections. By way of particular example, applicator 308 threadedly engages with an interior portion of neck 304.

Applicator 308 includes a first portion 312 and a second or tip portion 314. As illustrated, tip portion 314 is angled relative to a centerline first portion 312; however such is not required for practice of the present invention. Exemplary angles range from about zero to about ninety degrees, and is preferably about forty-five degrees relative to the centerline.

FIG. 4 illustrates yet another system 400 in accordance with additional embodiments of the invention. System 400 is similar to system 300, except system 400 includes an applicator 402, rather than applicator 308. Applicator 402 is similar to applicator 308, except applicator 402 does not include an angled tip.

Figure 5A:
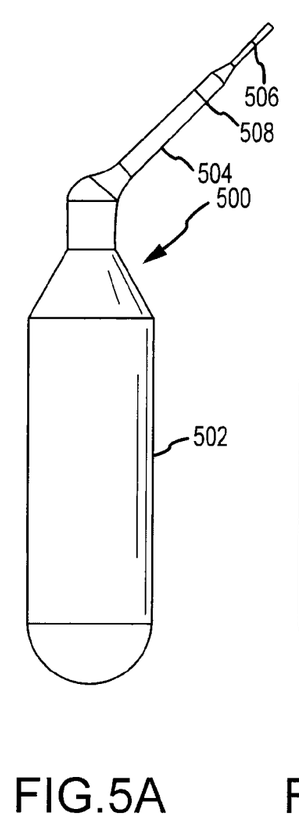
FIGS. 5A-5C illustrate, respectively, a left view, a front view, and a right view of an exemplary container for use in accordance with an exemplary embodiment of the invention.
Figures 5B, 5C:
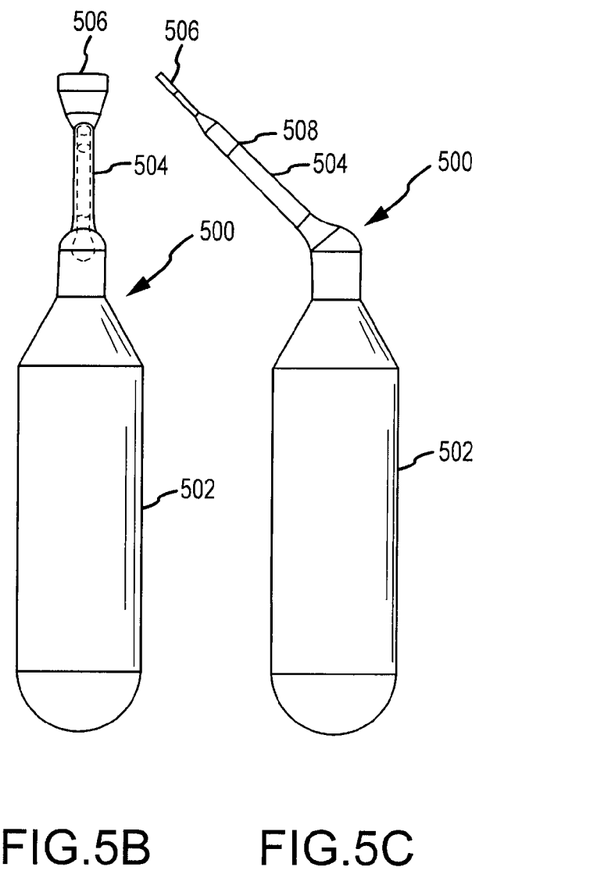

FIGS. 5A-5C illustrate left, front, and right views of yet another system 500 in accordance with various embodiments of the invention. System 500 is similar to systems 200-400, except system 500 is designed as a unitary system, having an integrated vessel 502 and spout 504, including a severable end 506 and scarred section 508.

Although not illustrated, systems in accordance with various embodiments of the invention may include tamper-resistant features. For example, system 200 may include a seal formed over neck 212, using, for example plastic or foil glued to or otherwise adhered to a top portion of neck 212. Alternatively, after spout portion 208 is attached to vessel portion 206, the two portions may be fused together using heat sealing and/or adhesive techniques.

Figure 6:
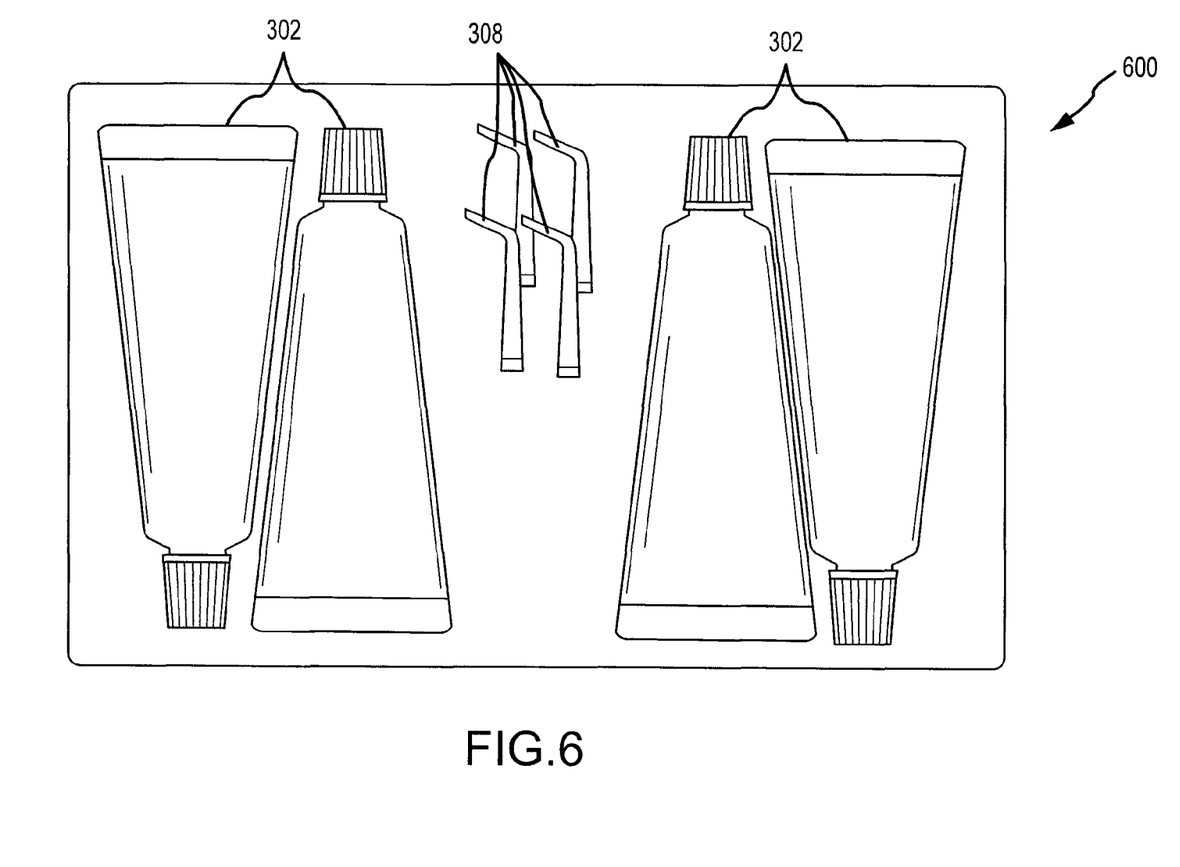
FIG. 6 illustrates an exemplary kit, including a plurality of systems, for use in accordance with yet another exemplary embodiment of the invention.

FIG. 6 illustrates a kit 600, including multiple systems, in accordance with yet additional embodiments of the invention. As illustrated, kit 600 includes four systems; however, systems in accordance with other embodiments of the invention may include a different number, e.g., 1, 2, 4, 7, 10, or the like number of systems.

Referring back to FIG. 1, providing a system, in accordance with step 102, can include any method now known or hereinafter devised for filling a container with a fluid. With reference to FIG. 2, a composition 202 can suitably be filled in one end of a container 204 and then sealed to maintain composition 202 within container 204. Alternatively, with momentary reference to FIG. 3, vessel 302 may be filled with composition 202 and then sealed with cap 306. In addition, filling container 204 with composition 202 may include filling a single and/or daily dose of composition 202, or multiple doses of composition 202.

Accessing composition 202 within container 204, in accordance with step 104, suitably comprises removal of an access, closure device or component from container 204. For example, in accordance with an exemplary embodiment, accessing composition 202 within container 204 comprises detachably removing an access component, e.g., end portion 222, to provide an access to composition 202.

Selectively applying composition 202 to a surface within an oral cavity, in accordance with step 106, can suitably include expulsing, transferring or otherwise forcing composition 202 from a vial 210 to an applicator portion 208 of container 204. For example, in accordance with an exemplary embodiment, composition 202 can be "squeezed" from an expulsion portion 206, into applicator portion 208, through an applicator tip 218, and onto a targeted surface within an oral cavity.

Regular and/or systematic use of methods in accordance with various embodiments of the invention result in measurably improved oral health.

SPECIFIC EXAMPLES

The following non-limiting examples illustrate improvement in oral health using a system, kit, and method in accordance with various embodiments of the invention. These examples are merely illustrative, and it is not intended that the invention be limited to the examples. Kits, systems, and compositions in accordance with the present invention may include the ingredients listed below as well as additional and/or alternative inert materials, preservatives, and other constituents typically found in compositions for promoting oral health. In the case where exemplary inert materials and/or preservatives are listed, these ingredients are merely exemplary, and it is understood that other similar ingredients may be substituted for the materials listed in the examples below.

Example 1

A pale light pink viscous gel, having a viscosity of about 40,000 cp, with cinnamon-clove characteristic odor and taste is formed by admixing the following ingredients, as described above, in the amounts shown. The composition was sealed in system 500, illustrated in FIG. 5.

TABLE 1

| Ingredient | Supplier | Weight % | Exemplary Wt % Range |
|---|---|---|---|
| Purified Water | Copacker | 91.504 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Cetylpyridinium Chloride | Dishman Pharmaceuticals | 0.100 | 0.001-1 |
| Zinc Gluconate USP | American International | 0.592 | 0.001-1.5 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

A clinical study, including 24 subjects, evaluating the efficacy of the composition of Table 1 was conducted. Subjects were scored at baseline, three weeks, and at six weeks using the Low and Silness Gingival Index (1963) (GI) and the Turesky Modification (1970) of the Quigley Hein Plaque Index (1962) (PI) indices. Plaque and calculus quality, thickness, maturity, and mass were also observed at these times.

At the end of a three-week period, there was an observed lessening or reduction of plaque quality, thickness, mass, and maturity; the lessening was greater (greater decrease) for those using the composition of Table 1, compared to a placebo. The observance that plaque quality was reduced is important because the presence of actively growing plaque bacteria (biofilm) is important in the development of inflammation, which leads to gingivitis and periodontitis.

In addition, at the end of the three-week period a lessening of the quality of calculus was also observed. A general improvement of gingival health was also observed. An extremely thin, slightly detached layer of epithelial cells was also found on the surface of attached gingival surfaces at the marginal ridge, close to the areas where plaque and tartar was likely disrupted off the teeth with subjects using the composition of Table 1, which indicated promotion of faster healing of gingival tissues.

Subjects at the end of the six-week period showed a statistically significant (p-value=0.05) greater performance than a placebo in both absolute (0.741) and percentage (40%) improvement in GI. There was also a directional improvement for PI in the absolute (1.805) and percent (49%) improvement for those using the formula of Table 1 compared to a placebo. There was also approximately a 50% reduction in plaque thickness at the end of the six-week period in about 73% of the subjects that were checked for plaque quality or thickness.

Example 2

A pale light pink viscous gel, having a viscosity of about 40,000 cp, with cinnamon-clove characteristic odor and taste is formed by admixing the following ingredients, as described above, in the amounts shown. The composition was sealed in system 500, illustrated in FIG. 5.

TABLE 2

| Ingredient | Supplier | Weight % | Exemplary Wt % Range |
|---|---|---|---|
| Purified Water | Copacker | 92.096 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Cetylpyridinium Chloride | Dishman Pharmaceuticals | 0.100 | 0.001-1 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

A clinical study, including 22 subjects, evaluating the efficacy of the composition of Example 2 was conducted. The Low and Silness Gingival Index (1963) (GI) for subjects using the formula of Table 2 for a six-week period showed a greater performance than a placebo in both absolute (0.405) and percentage (22%) improvement in GI. There was also a directional improvement for the Turesky Modification (1970) of the Quigley Hein Plaque Index (1962) (PI) in the absolute (1.489) and percent (41%) improvement for those using the formula of Table 2 compared to a placebo.

Example 3

A clinical study comparing V-MI scores of subjects using the composition of Table 1 was conducted to evaluate calculus dissolution. During the three-month study, the subjects were instructed to brush with toothpaste twice daily and apply the composition prior to retiring. Subjects did not receive professional cleaning just prior to participating in the study. The object of the study was to determine the efficacy of the composition and use thereof at removing calculus.

For 18 subjects using a system including the composition of Table 1, there was a statistically significant difference between original V-MI scores and V-MI scores (51%) after three months of treatment with the product, which indicates the system is effective at calculus dissolution.

Example 4

In another clinical study, 50 subjects received professional prophylaxis, including scaling and polishing, to remove supragingival calculus, extrinsic stain, and plaque deposits from the mandibular anterior teeth and initial V-MI measurements at 18 VM sites per subject were recorded prior to the study to evaluate calculus inhibition. Subjects were requested to refrain from flossing the mandibular 6 anterior teeth and place the composition between and around those teeth using system 500, illustrated in FIG. 5. At the end of a three-month period, VM-I measurements for the same teeth were recorded and analyzed using analysis of covariance. The V-MI scores at the end of the three-month period were statistically significantly lower (59%) than the initial V-MI scores. The study indicated that the system was effective at Calculus inhibition.

Example 5

A clinical study comparing V-MI scores of 40 subjects using the composition of Table 1 was conducted to evaluate disruption or dissolution of existing calculus bridges. During a three-month study, the subjects were instructed to brush with toothpaste twice daily and apply the composition prior to retiring.

At the end of the three-month study, a statistically significant difference (30% difference) of before and after scores of the subjects using the composition of Table 1 was observed. In addition, a statistically significant difference (26% difference) of the 40 subjects compared to 40 subjects using a placebo was observed, and a statistically significant difference (99%) between the change in scores before and after the study between the placebo group and the group using a system including the composition of Table 1.

Example 6

A clinical study comparing Gingivitis Index (GI), Plaque Index (PI), and Bleeding Index (BI) scores using the composition of Table 1 was conducted. Forty-five subjects were evaluated over a period of three months and 39 subjects were evaluated over a period of six months. During the study, the subjects were instructed to brush with toothpaste twice daily and apply the composition prior to retiring. The subjects were asked not to use other oral hygiene products. After a baseline examination, all subjects received dental prophylaxis.

At the end of the three-month period, a 16% reduction in GI was observed, a 26% reduction in PI was observed, and a 68% reduction in BI was observed. At the end of the six-month period, a 32% reduction in GI was observed, a 33% reduction in PI was observed, and a 78% reduction in BI was observed. All reductions are statistically significant (p-Value<0.01) using the Mann-Whitney Rank Sum Test.

Example 7

A pale light pink viscous gel, having a viscosity of about 40,000 cp, with cinnamon-clove characteristic odor and taste is formed by admixing the following ingredients, as described above, in the amounts shown. The composition was sealed in system 500, illustrated in FIG. 5.

TABLE 3

| Ingredient | Supplier | Weight % | Exemplary Wt % Range |
|---|---|---|---|
| Purified Water | Copacker | 91.604 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Zinc Gluconate USP | American International | 0.592 | 0.001-1.5 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

A clinical study comparing Gingivitis Index (GI), Plaque Index (PI), and Bleeding Index (BI) scores using the composition of Table 3 was conducted. Fifty-one subjects were evaluated over a period of three months and forty-three people were evaluated over a period of six months. During the study, the subjects were instructed to brush with toothpaste twice daily and apply the composition prior to retiring. The subjects were asked not to use other oral hygiene products. After a baseline examination, all subjects received dental prophylaxis.

At the end of the three-month period, a 11% reduction in GI was observed, a 17% reduction in PI was observed, and a 58% reduction in BI was observed. At the end of the six-month period a 16% reduction in GI was observed, a 21% reduction in PI was observed, and a 52% reduction in BI was observed. All reductions are statistically significant (p-Value<0.01) using the Mann-Whitney Rank Sum Test.

Example 8

A clinical study comparing Gingivitis Index (GI), Plaque Index (PI), and Bleeding Index (BI) scores using the composition of Table 2 was conducted. Fifty subjects were evaluated over a period of three months and 44 people were evaluated over a period of six months. During the study, the subjects were instructed to brush with toothpaste twice daily and apply the composition prior to retiring. The subjects were asked not to use other oral hygiene products. After a baseline examination, all subjects received dental prophylaxis.

At the end of the three-month period, a 18% reduction in GI was observed, a 25% reduction in PI was observed, and a 65% reduction in BI was observed. At the end of the six-month period, a 31% reduction in GI was observed, a 32% reduction in PI was observed, and a 75% reduction in BI was observed. All reductions are statistically significant (p-Value<0.01) using the Mann-Whitney Rank Sum Test.

Example 9

A clinical study comparing V-MI scores using a placebo and the compositions of Tables 1 and 4 was conducted. Data was recorded at baseline, 40 days and 90 days. Subjects were provided coded tubes of the gel formulation to which they were assigned. The subjects were instructed to apply the gel daily, once before going to bed. The gel was applied between the teeth at the gum margin all along the arch. After applying, the subjects were instructed to spit out any excess and not to eat or drink prior to an extended period of rest.

TABLE 4

| Ingredient | Supplier | Weight % | Exemplary Wt % Range |
|---|---|---|---|
| Purified Water | Copacker | 91.504 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Cetylpyridinium Chloride | Dishman Pharmaceuticals | 0.100 | 0.001-1 |
| Zinc Gluconate USP | American International | 1.184 | 0.001-1.5 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

After 90 days, users of the composition of Table 4 had 19% better V-MI scores, and users of the composition of Table 1 had 10% better V-MI scores. Following treatment, users of the composition of Table 1 had 0.31 better absolute V-MI scores and users of the composition of Table 4 had 0.32 better absolute V-MI scores.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. These and other changes or modifications are intended to be included within the scope of the present invention, as set forth in the following claims.

We claim:

1. A method to measurably improve an oral health index comprising:
    providing a system, including a composition within a container, wherein the composition consists of active ingredients, consisting of zinc gluconate and cetylpyridinium chloride, and a carrier consisting of a thickener selected from the group consisting of hydroxyethylcellulose, hydroxypropyl methylcellulose, carrageenan, sugar, guar gum, methylcellulose, and methyethylecellulose, water, a humectant, one or more essential oils, optionally one or more flavorants, optionally one or more sweeteners, and optionally one of more colorants,
    wherein the composition has a viscosity between, about 30,000 centipoise and about 50,000 centipoise, and wherein the container comprises a vial and an applicator portion sealably coupled to the vial;
    accessing the composition by expulsing the composition from the vial and through the applicator portion; and
    selectively applying the composition using the applicator portion onto a surface within an oral cavity to measurably improve a combination of a gingivitis index (GI), a plaque index (PI), a bleeding index (BI), and a Volpe-Manhold index (V-MI).

2. The method of claim 1, wherein the V-MI index is measurably improved by 10% to 59%.

3. The method of claim 1, wherein the BI is measurably improved by 68% to 78%.

4. The method of claim 1, wherein the humectant comprises glycerin.

5. The method of claim 1, wherein the viscosity of the composition is about 35,000 to about 45,000 centipoise.

6. The method of claim 1, wherein said active ingredients consist of about 0.001 wt % to about 1.5 wt % zinc gluconate and about 0.001 wt % to about 1 wt % cetylpyridinium chloride.

7. A method to measurably improve an oral health index comprising:
    providing a kit, including a plurality of systems, wherein each system includes a composition within a container and wherein the composition consists of active ingredients, consisting of zinc gluconate and cetylpyridinium chloride, and a carrier consisting of a thickener selected from the group consisting of hydroxyethylcellulose, hydroxypropyl methylcellulose, carrageenan, sugar, guar gum, methylcellulose, and methyethylecellulose, water, a humectant, one or more essential oils, optionally one or more flavorants, optionally one or more sweeteners, and optionally one of more colorants, and has a viscosity between about 30,000 and about 50,000 centipoise, and wherein the container comprises a vial and an applicator portion sealably coupled to the vial;
    accessing the composition by expulsing the composition from the vial and through the applicator portion; and
    selectively applying the composition using the applicator portion to a surface within an oral cavity to measurably improve a combination of a gingivitis index (GI) by 0.741, a plaque index (PI) by 1.805, a bleeding index (BI), and a Volpe-Manhold index (V-MI) by 0.31.

8. The method of claim 7, wherein the GI index is measurably improved by 16%.

9. The method of claim 7, wherein the V-MI is improved by 30%.

10. The method of claim 7, wherein the viscosity of the composition is about 35,000 to about 45,000 centipoise.

11. The method of claim 7, wherein said thickener is hydroxyethylcellulose.

12. The method of claim 7, wherein the PI is improved by 26%.

13. A method to measurably improve an oral health index comprising:
    providing a composition within a container, wherein the composition consists of active ingredients, consisting of zinc gluconate and cetylpyridinium chloride, and a carrier consisting of a thickener selected from the group consisting of hydroxyethylcellulose, hydroxypropyl methylcellulose, carrageenan, sugar, guar gum, methylcellulose, and methyethylecellulose, water, a humectant, one or more essential oils, optionally one or more flavorants, optionally one or more sweeteners, and optionally one of more colorants, and has a viscosity of about 30,000 to about 50,000 centipoise, and wherein the container comprises a vial and an applicator portion sealably coupled to the vial; and selectively applying the composition using the applicator portion to a surface within an oral cavity to measurably improve a combination of a gingivitis index (GI) by 16%, a plaque index (PI) by 26%, a bleeding index (BI) by 68%, and a Volpe-Manhold index (V-MI) by 10%.

14. The method of claim 13, wherein the GI is improved by 40%.

15. The method of claim 13, wherein the PI is improved by 49%.

16. The method of claim 13, wherein the viscosity of the composition is 35,000 to about 45,000 centipoise.

17. The method of claim 13, wherein said composition has a plurality of essential oils.

18. The method of claim 13, wherein said selectively applying step is performed before an extended period of rest.

19. The method of claim 13, wherein the step of providing a composition within a container comprises providing a container including a removable cap and a removable spout.

20. The method of claim 13, wherein the composition includes about 0.001 weight percent to about 1 weight percent cetylpyridinium chloride and about 0.001 weight percent to about 1.5 weight percent zinc gluconate.

\* \* \* \* \*